(12) United States Patent
Poland et al.

(10) Patent No.: US 12,070,484 B2
(45) Date of Patent: *Aug. 27, 2024

(54) TEVERELIX-TFA COMPOSITION (71) Applicant: Antev Limited, London (GB)

(72) Inventors: Guy Poland, Bristol (GB); Francois Boutignon, Clermont-Ferrand (FR)

(73) Assignee: Antev Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/740,743

(22) Filed: May 10, 2022

(65) Prior Publication Data
US 2022/0273758 A1    Sep. 1, 2022

Related U.S. Application Data (63) Continuation of application No. 17/254,864, filed as application No. PCT/EP2019/067728 on Jul. 2, 2019, now Pat. No. 11,357,818.

(30) Foreign Application Priority Data

Jul. 5, 2018 (EP) ..................... 18181945

(51) Int. Cl.
*A61K 38/09* (2006.01)
*A61K 9/08* (2006.01)
*A61K 47/12* (2006.01)
*A61P 5/00* (2006.01)
*A61P 13/00* (2006.01)
*A61P 35/00* (2006.01)

(52) U.S. Cl.
CPC ................ *A61K 38/09* (2013.01); *A61K 9/08* (2013.01); *A61K 47/12* (2013.01)

(58) Field of Classification Search
CPC .......... A61K 38/09; A61K 9/08; A61K 47/12; A61K 2300/00; A61P 13/00; A61P 5/00; A61P 35/00
See application file for complete search history.

(56) References Cited

U.S. PATENT DOCUMENTS

2003/0044463 A1* 3/2003 Deghenghi ............ A61K 47/12
                                                          514/10.6
2021/0052692 A1* 2/2021 Larsen ...................... A61P 5/30

* cited by examiner

*Primary Examiner* — Julie Ha
(74) *Attorney, Agent, or Firm* — Fox Rothschild LLP (57) ABSTRACT Provided is a teverelix-TFA composition having a molar ratio of teverelix to trifluoroacetate composition of at least 1:2.2. Such a molar ratio will prevent undesirable gel-formation and provide a homogenous suspension, whereby a unique bioavailablity of teverelix is obtained.

14 Claims, 6 Drawing Sheets

Microscopy of suspension A1

Fig. 1a

Microscopy of suspension B1

Fig. 1b

Microscopy of suspension C1

Fig. 1c

Microscopy of suspension D1

Fig. 1d

Microscopy of suspension E1

Fig. 1e

Microscopy of suspension F1

Fig. 1f

Microscopy of suspension G1

TEVERELIX-TFA COMPOSITION

This Application is a Continuation of application Ser. No. 17/254,864 filed on Dec. 22, 2020. Application Ser. No. 17/254,864 is a National Phase of International Patent Application No. PCT/EP2019/067728, filed Jul. 2, 2019, and claims priority to European Patent Application No. 18181945.9 filed on Jul. 5, 2018. The entire contents of these applications are incorporated herein by reference in their entirety.

The present invention relates to a teverelix-TFA composition.

Teverelix is a synthetic gonadotropin-releasing hormone antagonists (GnRH antagonists) that compete with the endogenous neurohormone GnRH (otherwise known as luteinizing hormone releasing hormone, LHRH) for binding to its receptors in the anterior pituitary gland. By decreasing or blocking GnRH action, the GnRH antagonist suppress release from the anterior pituitary gland of follicle stimulating hormone (FSH) and luteinizing hormone (LH).

Both FSH and LH are involved in normal reproductive function. In females, FSH stimulates the growth of immature Graafian follicles to maturation, whereas changes in LH levels control ovulation. In males, on the other hand, FSH plays an important role in spermatogenesis and LH stimulates production of testosterone in the testes.

Accordingly, teverelix is suitable for treatment of hormone-dependent conditions such as benign prostatic hypertrophy, hormone-dependent prostate cancer, endometriosis and uterine myomas.

Since teverelix (Ac-D-Nal-D-pClPhe-D-Pal-Ser-Tyr-D-Hci-Leu-Lys(iPr)-Pro-D-Ala-$NH_2$) is a hydrophobic peptide it has a tendency of forming gels in the presence of many counter-ions. This problem has been solved in WO 2003/022243 which discloses that the formation of a gel may be prevented by contacting the teverelix peptide with a counter-ion, e.g. trifluoroacetate (TFA), at a molar ratio of at least 1:1.6 of peptide to counter-ion, thereby providing a fluid, milky microcrystalline aqueous suspension of the teverelix-salt (e.g. teverelix-TFA).

According to WO 2003/022243, a ratio of teverelix to the counter-ion trifluoroacetate of at least 1:1.6 is essential in order to ensure the desired microcrystalline suspension is obtained, otherwise a gel will be formed. However, the inventors of the present invention has found that such molar ratios will result in both undesirable gel-formation and in suspensions which are not homogenous. This is a problem, not only because such suspensions will be difficult to inject, but also because the bioavailability of the teverelix peptide is compromised since the gel interferes with the desired sustained action of said peptide.

Accordingly there is a demand to provide a new teverelix-TFA composition that can provide a homogeneous microcrystalline aqueous suspension of teverelix, which will provide a sustained release of the teverelix.

This and further aspects are achieved according to the present invention by providing a teverelix-TFA composition having a molar ratio of teverelix to trifluoroacetate of at least 1:2.2.

Within the content of the present invention the term "molar ratio of teverelix to trifluoroacetate" refers to the molar relationship between teverelix and trifluoroacetate, where the first number of the molar ratio is the mol content of teverelix in the composition and the second number refers to the mol content of TFA in the composition. For instance, a molar ratio of 1:2.2 means that for each mol teverelix in the composition, said composition comprises 2.2 mol TFA, and a molar ratio of at least 1:2.2 means that for each mole teverelix in the composition, the composition comprises at least 2.2. mol trifluoroacetate (TFA).

The inventors of the present invention have found that when the molar ratio of teverelix to trifluoroacetate is at least 1:2.2 composition will comprise both soluble and insoluble teverelix, thereby providing a unique bioavailablity of teverelix.

For the teverelix to be absorbed in the body, said ingredient must be present in the form of solution at the site of absorption. Various techniques are used for the enhancement of the solubility of poorly soluble drugs, such as teverelix, however the inventors have found that crystal engineering, in which the teverelix and trifluoroacetate provides an organisation of the teverelix peptide and its counter-ion in a crystalline structure provides an effective sustained release of teverelix, having improve physicochemical properties (e.g., solubility and stability), and improve efficacy (e.g., bioavailability).

Without being bound by theory, the soluble teverelix is in the form of an aqueous solution, and in some situations a gel. The presence of a gel will inhibit any freely aqueous teverelix and therefore prevent, or at least reduce, immediate release. The insoluble teverelix is in the form of microcrystals. Said microcrystals will prevent gel formation, therefore "unlocking" the aqueous teverelix. Over time the TFA in the composition according to the invention will be absorbed by the body, lowering the ratio, so the microcrystals subsequently turn in to gel, which forms the slow release depot. Thus, the non-gel-soluble teverelix is immediately available, providing an almost immediate onset of action, and the gel-soluble and insoluble teverelix (microcrystals) will assist in providing a sustained release of teverelix. Accordingly the composition according to the invention provides a soluble-insoluble transition at the administration site, and accordingly a sustained release of teverelix.

Thus, the composition according to the invention has both an immediate onset of action leading to a fast suppression of the gonadotropins, but also a sustain release of antagonist thereby ensuring that the subject maintains a therapeutically effective concentration in the blood plasma. This will not only provide a more reliable composition for the treatment of gonadotropin relates diseases and conditions, but also improve patient compliances as fewer administrations (e.g. injections) are required.

The molar ratio of teverelix to trifluoroacetate is preferably at least 1:2.2, i.e. for each mole of teverelix, the composition comprises at least 2.2. mol trifluoroacetate (TFA), and even more preferred at least 1:2.4 as this will provide an aqueous pharmaceutical formulation that may be used directly, i.e. the formulation is ready-to-use.

Since teverelix is deamidated when placed in contact with water and acid, undesirable degradation products (impurities) will appear within the composition/formulation during storage. Said impurities may influence quality, safety and efficacy of the teverelix composition/formulation, thereby potentially causing serious health hazards.

The inventors of the present invention has found that the level of impurities are kept at an acceptable level, when the molar ratio of teverelix to TFA is at or below 1:2.8, i.e. when the molar content of TFA is at or below 2.8 per mol teverelix. Thus, the optimal molar ratio in the composition according to the invention is preferably between 1:2.2 (or 1:2.4) and 1:2.8.

The composition according to the invention is especially suitable for treating a condition such as prostate cancer through a suppression of gonadotropins such as testosterone and dihydrotestosterone (DHT). Since such a composition both will have an immediate onset of action leading to a profound suppression of testosterone, and a sustain release of antagonist thereby ensuring that the subject maintains chemically castrated, the composition is both valuable in the treatment of patients with prostate cancer where fast control of disease is needed and for patients where only sustained release is relevant.

The composition according to the invention may however equally well be used to at least partially ameliorating other diseases or condition related to the release of a gonadotropin hormone. Said disease or condition may be benign prostatic hyperplasia; acute urinary retention; endometriosis; a cancer such as prostate, breast, or cervical cancer; chemical castration; a hormone imbalance; an androgen-sensitive condition; an estrogen sensitive condition; or a combination thereof.

The present invention also relates to an aqueous pharmaceutical formulation, preferably a milky, microcrystalline homogeneous aqueous suspension, consisting of or comprising the teverelix-TFA composition according to the invention with a molar ratio of teverelix to trifluoroacetate of at least 1:2.2, preferably at least about 1:2.4. In a preferred embodiment of the aqueous pharmaceutical formulation the molar ratio of teverelix to trifluoroacetate is below 1:2.8, i.e. per 1 mol teverelix the formulation contains 2.8 mol TFA, or less.

If desired, the aqueous pharmaceutical formulation may contain an isotonic agent, such as mannitol and/or a pharmaceutically acceptable excipient.

In a simple and preferred embodiment according to the invention, the teverelix-TFA composition is provided as a unit dosage having a molar ratio of teverelix to TFA which is at least 1:2.2 and even more preferred about 1:2.4 thereby ensuring that the provided suspension contains substantially no gel, or at least so small concentrations of gel that the suspension can be used for injections.

Accordingly, another aspect of the invention features a package e.g. a syringe or vial, filled with a unit dosage of the teverelix-TFA composition. Within the context of the present invention the term "unit dosage" is the amount of an active ingredient (teverelix) administered to a patient in a single dosage. Said unit dosages is e.g. placed in a suitable syringe in order to provide an easy administration.

In one embodiment unit dosage provides a final aqueous teverelix-TFA formulation having a molar ratio of teverelix to counter-ion of 1:2.4. Preferably the concentration of teverelix is between 30 mg/ml and 100 mg/ml, and even more preferred between 45 mg/ml and 90 mg/ml, e.g. about 75 mg/ml. The concentration of teverelix may in some situations be higher than about 100 mg/ml. The volume may be between 0.4 ml and 1.6 ml, e.g. about 1.2 ml. Injection given subcutaneous and/or intramuscularly at this concentration and volume, has proven to only provide a mild injection site reaction.

EXAMPLES

In order to establish the influence of the molar ratio of teverelix to the counter-ion trifluoroacetate a number of tests were performed.

Example 1: Preparation of Teverelix-TFA Compositions with Different Molar Ratio A custom-manufactured batch of teverelix with low TFA content, Batch A, was obtained. The characteristics of the batch are shown in table 1.

TABLE 1

| | |
|---|---|
| Purity | 99.3% |
| Teverelix content | 85.56 weight-% |
| TFA content | 10.9 weight-% |
| Acetate content | 0.3 weight-% |
| Water content | 4.3 weight-% |

If a initial composition, composition A, containing 75 mg teverelix is desired then 88.28 mg of batch A has to be used, calculated as follows:

$$\frac{75 \text{ mg teverelix}}{99.3/100(\% \text{ purity}) \times 85.56/100(\% \text{ teverelix content})} = 88.28 \text{ mg}$$

The molar ratio of teverelix to TFA in composition A can then be calculated: 88.28 mg×10.9/100 (TFA content in %)=9.62 mg Since the molar mass of TFA, is 114 g/mol, and the molar mass of teverelix, $M_{rev}$, is 1459 g/mol, the molar concentration in the 75 mg teverelix composition of TFA can be calculated to 0.084 mmol and the molar concentration of teverelix to 0.051 mmol. Thus, the molar ratio of teverelix to TFA in composition A, is 1:1.64.

In order to prepare a number of different aqueous teverelix-TFA compositions with different molar ratios, twenty-one samples containing 44.14 mg+5% (41.93 to 46.35 mg) of composition A were accurately weighed in 2 ml glass tubes having a cap through which a reconstitution solution could be added by means of a micropipette.

Seven TFA solutions containing TFA in 5% mannitol were prepared using a TFA composition obtained from Acros Organics, Geel, Belgium. Said TFA composition were 99% pure and had a density of 1.535 g/ml. The respective reconstitution solutions are shown in Table 2.

TABLE 2

| Solution | A | B | C | D | E | F | G |
|---|---|---|---|---|---|---|---|
| TFA mol/L | 0 | 0.01 | 0.023 | 0.036 | 0.049 | 0.062 | 0.075 |

The respective aqueous teverelix-TFA compositions were prepared by adding 0.5 ml of each of the above reconstitution solutions though the cap of the twenty-one glass tubes containing 44.14 mg+5% (41.93 to 46.35 mg) of composition A using a micropipette, i.e. three aqueous teverelix-TFA compositions having the same molar ratio were prepared. The mixtures were stirred using a vortex for 1 minute, and the solutions were observed visually for 10 minutes in order to establish if the desired fluid, milky microcrystalline homogeneous aqueous suspension of the teverelix-TFA, were obtained, or if a gel was formed instead. The results are summarised in Table 3 below:

TABLE 3

| Tubes | Molar ratio | Formation of gel | Microcrystalline formation | Formation of milky suspension | homogeneous suspension |
|---|---|---|---|---|---|
| A1, A2, A3 | 1:1.64 | yes | no | no | — |
| B1, B2, B3 | 1:1.85 | yes | no | no | — |
| C1, C2, C3 | 1:2.1 | no | yes | yes | no |
| D1, D2, D3 | 1:2.36 | no | yes | yes | yes |
| E1, E2, E3 | 1:2.61 | no | yes | yes | yes |
| F1, F2, F3 | 1:2.86 | no | yes | yes | yes |
| G1, G2, G3 | 1:3.12 | no | yes | yes | yes |

The microcrystalline content of the aqueous teverelix-TFA compositions in the No. 1 test tubes were further observed under a polarized light microscope supplied by Realux, France.

The results for the respective molar ratio are shown in FIG. 1a-FIG. 1g. From these observations it is clear that microcrystalline formation is not observed for the molar ratios of 1:1.85 and below, thus the molar ratio of teverelix to the counter-ion TFA has to be above 1:1.85 in order for the desired microcrystalline formation to be initiated.

Furthermore, as is evident from table 3, a homogeneous suspension of teverelix-TFA was not obtained with a molar ratio at or below 1:2.1, thus it is accordingly preferred that the molar ratio in the aqueous teverelix-TFA suspension is above 1:2.2 and preferably even higher such as at least 1:2.36 (~1:2.4), otherwise said composition cannot be administered via an injection.

Example 2: Content of Soluble Teverelix and Insoluble Teverelix in Relation to the Molar Ratio In order to determine the content of soluble teverelix in relation to insoluble teverelix in the respective test tubes, the No. 2 and No. 3 test tubes for each molar ratio were centrifuged at 10,000 rpm for 10 to 20 minutes, and the concentration of teverelix in the supernatant and pellet were measured using a HPLC analysis.

The chromatographic conditions for the HPLC analysis is shown in table 4.

TABLE 4

| Column | Type (Aptys N°) | Lichrospher 100 RP18 (N°128) |
|---|---|---|
| | Particles size | 5 μm |
| | Diameter | 4 mm |
| | Length | 12 5 mm |
| Pre-Column | Type | Lichrocart 100 RP18 |
| | Particles size | 5 μm |
| | Diameter | 4 mm |
| | Length | 4 mm |
| Mobile Phase | | Acetonitrile/Water/TFA (35:65:0.1 V/V/V) |
| Injector cleaning | | Acetonitrile/Water (50:50 V/V) |
| Flow | | 1.0 mL/min |
| Pressure | | Approx. 65 bars |
| Oven Temperature | | 30° C. |
| Wavelength | | 210 nm |
| Injection volume | | 10 μL |
| Injector temperature | | 20° C. |
| Retention time of Teverelix | | Approx. 5.6 min |
| Run time | | 10 min |

Two 100% standards were prepared by weighing 59.9 mg teverelix acetate (hatch 080113) in a volumetric flask and completing the volume to 100 ml with water:acetonitrile 65:35 v/v. 10 ml of this solution were completed to 50 ml with the same solvent, providing a concentration of 0.1 mg/ml teverelix peptide.

A 1% standard solution was prepared by diluting 2 ml of the 100% standard to 200 ml with the same solvent providing a concentration of 0.001 mg/ml teverelix peptide.

Internal standardization was carried out using the two 100% standards. The 1% standard was used to check the linearity of the response. Recovery with the 100% standard must be in the interval 95%-105%.

The pellet obtained after centrifugation was solubilised in water:acetonitrile 65:35 v/v, and the volume was completed to 100 mL with the same solvent. This solution was diluted by 5 (10 mL in 50 mL) and HPLC was performed.

The supernatant was transferred to a volumetric flask and the volume was completed to 100 mL with the same solvent, i.e. water:acetonitrile 65:35 v/v. This solution was diluted by 5 (10 mL in 50 mL) and HPLC was performed. The results of the HPLC analysis is shown in table 5.

TABLE 5

| Test tube | Molar ratio | Supernatant - Teverelix concentration (mg/ml) | Pellet - Teverelix concentration (mg/ml) |
|---|---|---|---|
| A2 | 1:1.64 | 52.0 | N/A |
| A3 | 1:1.64 | 58.5 | N/A |
| B2 | 1:1.85 | 57.2 | N/A |
| B3 | 1:1.85 | 60.3 | N/A |
| C2 | 1:2.1 | 25.9 | 26.9 |
| C3 | 1:2.1 | 26.1 | 25.5 |
| D2 | 1:2.36 | 9.4 | 39.3 |
| D3 | 1:2.36 | 8.3 | 44.9 |
| E2 | 1:2.61 | 5.4 | 50.8 |
| E3 | 1:2.61 | 7.2 | 51.6 |
| F2 | 1:2.86 | 3.7 | 56.2 |
| G3 | 1:2.86 | 3.6 | 58.4 |
| G2 | 1:3.12 | 1.5 | 53.6 |
| G3 | 1:3.12 | 1.2 | 58.4 |

Figure 1A:
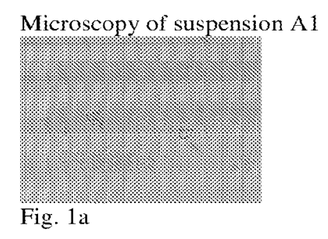
Figure 1B:
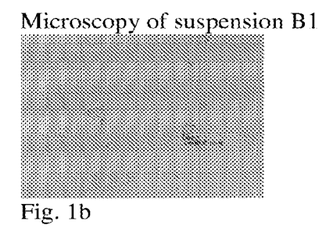
Figure 1C:
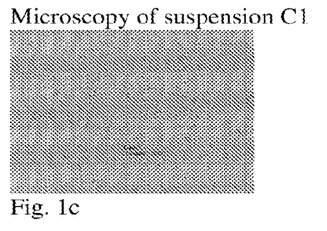
Figure 1D:
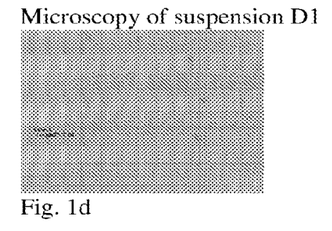
Figure 1E:
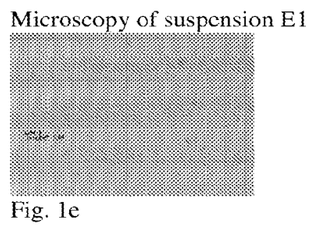
Figure 1F:
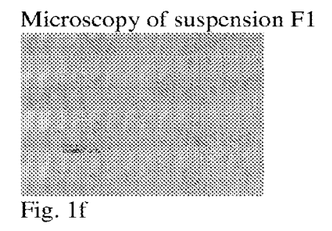
Figure 1G:
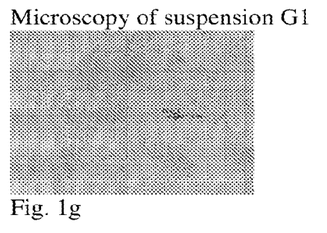
Figure 2:
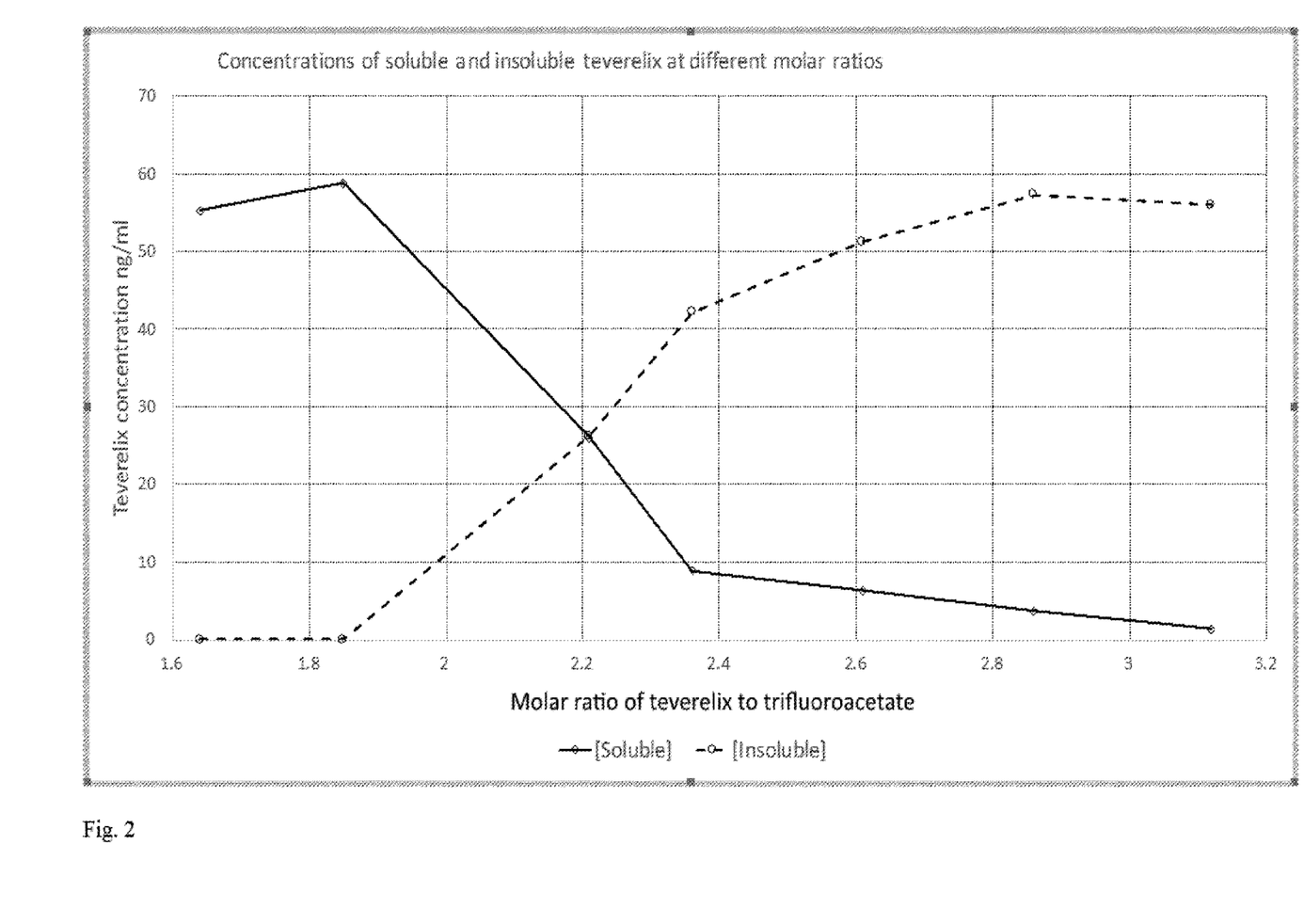
Figure 3:
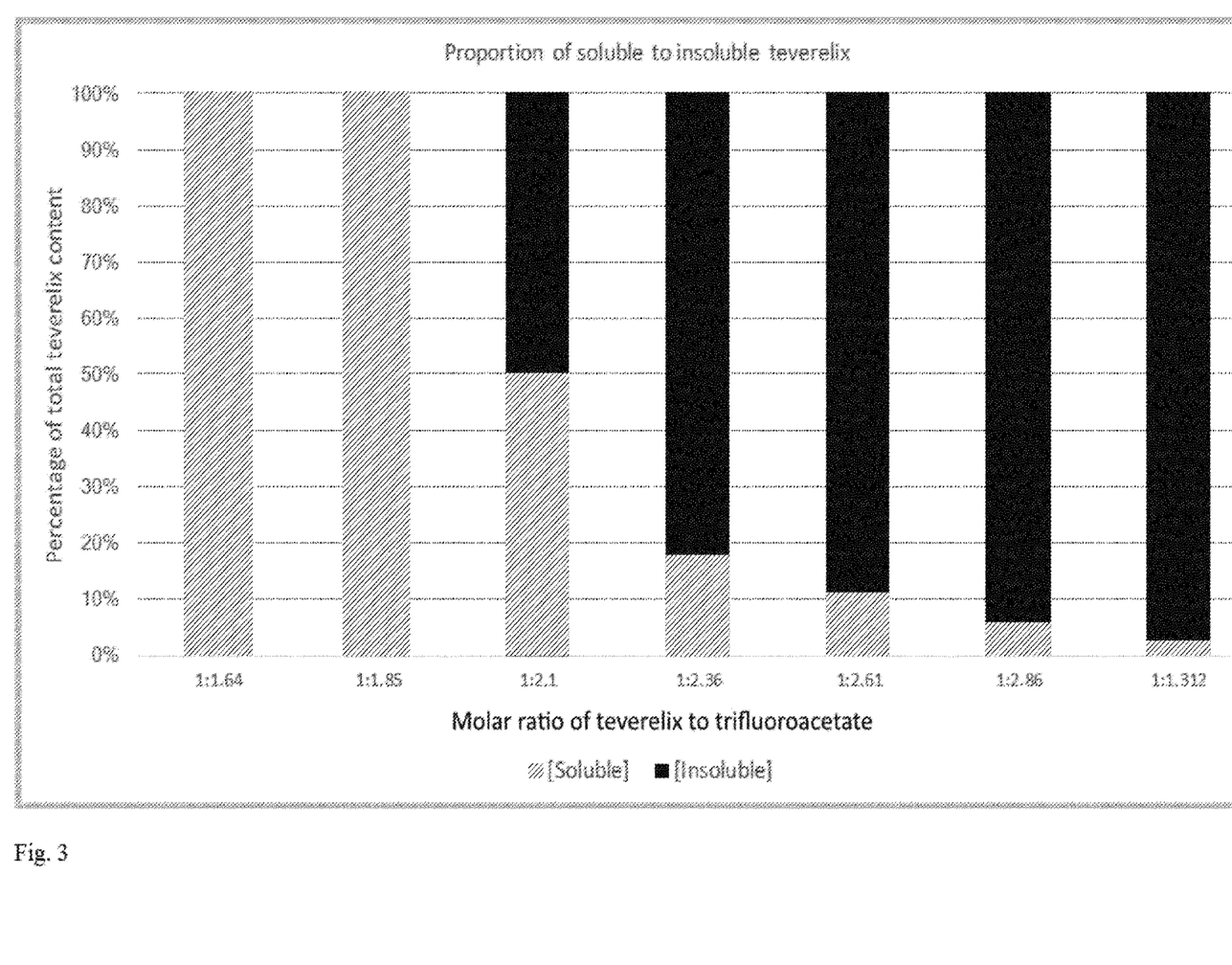

The average concentrations of each molar ratio was calculated, see table 6, and the results are depicted in FIGS. 2 and 3.

TABLE 6

| Test tube | Molar ratio | Supernatant - Average Teverelix concentration (mg/ml) | Pellet - Average Teverelix concentration (mg/ml) | Total (pellet + supernatant) Teverelix concentration (mg/ml) |
|---|---|---|---|---|
| A | 1:1.64 | 55.3 | N/A | 55.3 |
| B | 1:1.85 | 58.8 | N/A | 58.8 |
| C | 1:2.1 | 26.0 | 26.2 | 52.2 |
| D | 1:2.36 | 8.9 | 42.1 | 51.0 |
| E | 1:2.61 | 6.3 | 51.2 | 57.5 |
| F | 1:2.86 | 3.7 | 57.3 | 61.0 |
| G | 1:3.12 | 1.4 | 56.0 | 57.4 |

As is evident from table 5, and 6, and FIGS. 2 and 3, the degree of insoluble teverelix increases when the amount of trifluoroacetate increases in relation to teverelix, thus at a molar ratio of 1:2.1, about 50% of the pharmaceutical formulation consist of insoluble teverelix, whereas the amount of insoluble (microcrystalline) teverelix is about 80% at a molar ratio of 1:2.2. and about 82% at a molar ratio a molar ratio of 1:2.36 (~1:2.4) in the pharmaceutical formulation.

Example 3: Plasma Concentration in Relation to the Molar Ratio

In order to evaluate the relevance of the molar ratio on the plasma concentration of teverelix, five glass vials containing different molar ratios were prepared as discussed in example 1, and the test tubes comprising the aqueous teverelix-TFA compositions shown in table 7 were provided:

TABLE 7

| Tube | I | II | III | IV | V |
|---|---|---|---|---|---|
| Molar ratio | 1:1.64 | 1:2.1 | 1:2.36 | 1:2.61 | 1:2.86 |

Five rats were tested with each molar ratio. Each rat was injected with 60 µl of the respective solutions using a 25 mm 21G luer 6% regular bevel needle (obtainable from Terumo, Leuven, Belgium) and 100 µl luer slip syringe (obtainable from Hamilton Company, Reno, USA). Plasma concentrations were measured prior to administration, then at 1 h, 6 h, 24 h, 48 h, 7 days, 10 days, 14 days, 21 days and 28 days following administration.

Figure 4:
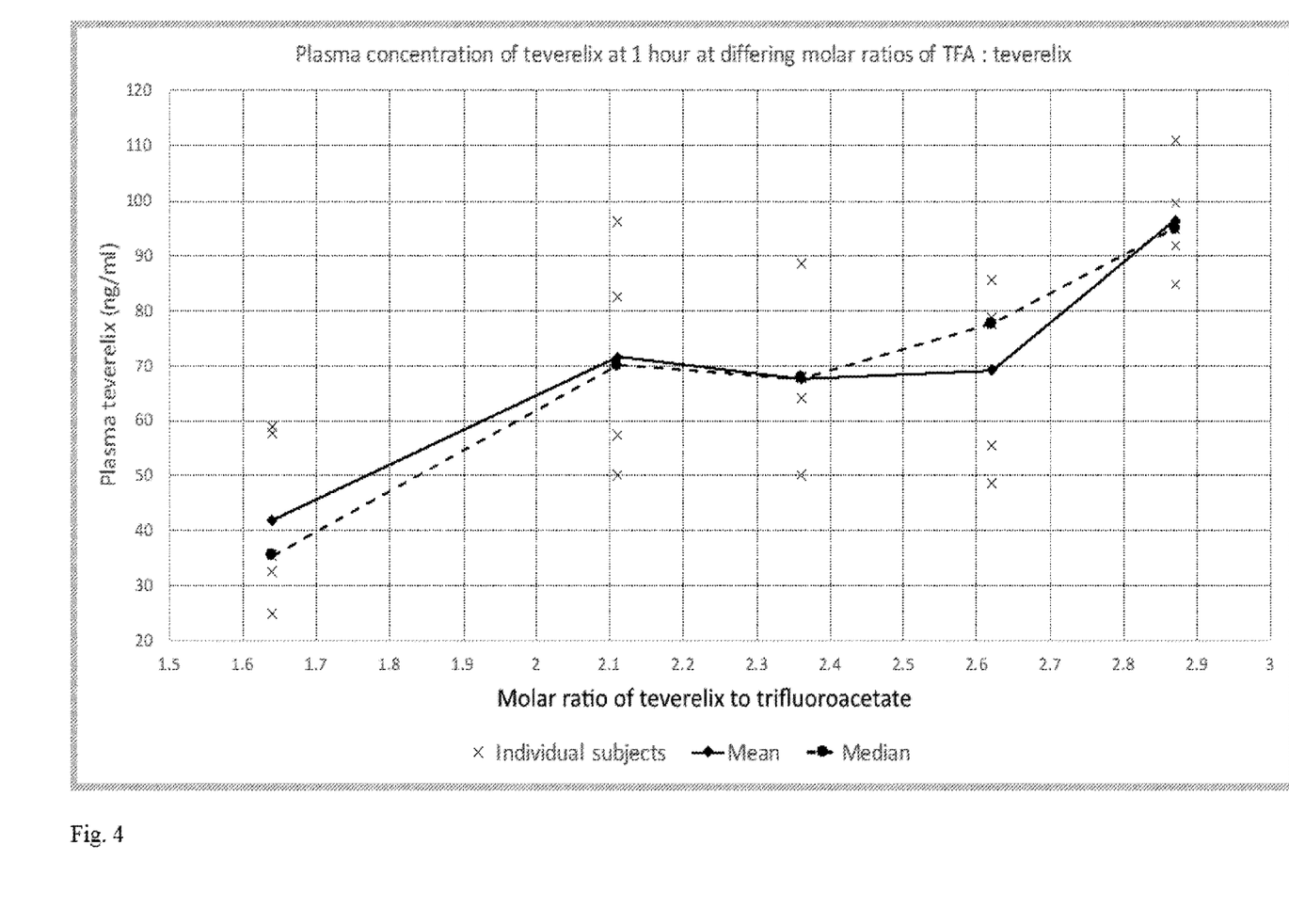

The peak plasma concentrations, Cmax, of teverelix after injection to each individual rat are shown in table 8, and depicted in FIG. 4.

TABLE 8

| Test tube | Molar ratio | Cmax | Cmax | Cmax | Cmax | Cmax | Cmax mean | Cmax median |
|---|---|---|---|---|---|---|---|---|
| I | 1:1.64 | 57.6 | 58.8 | 35.4 | 32.5 | 25 | 41.86 | 35.4 |
| II | 1:2.1 | 96 | 82.6 | 57.4 | 50.1 | n.a. | 76.525 | 70 |
| III | 1:2.36 | 67.6 | 50 | 67.9 | 64.2 | 88.6 | 67.66 | 67.6 |
| IV | 1:2.61 | 78.8 | 48.6 | 85.5 | 77.5 | 55.3 | 69.14 | 77.5 |
| V | 1:2.86 | 111 | 99.7 | 94.9 | 91.9 | 84.8 | 96.46 | 94.9 |

As is clear from these results the Teverelix Cmax increases until a molar ratio of 1:2.1 after which the plasma concentration is substantially stable.

The plasma concentration over a four week period, was also measured by taking blood samples at regular intervals.

Figure 5:
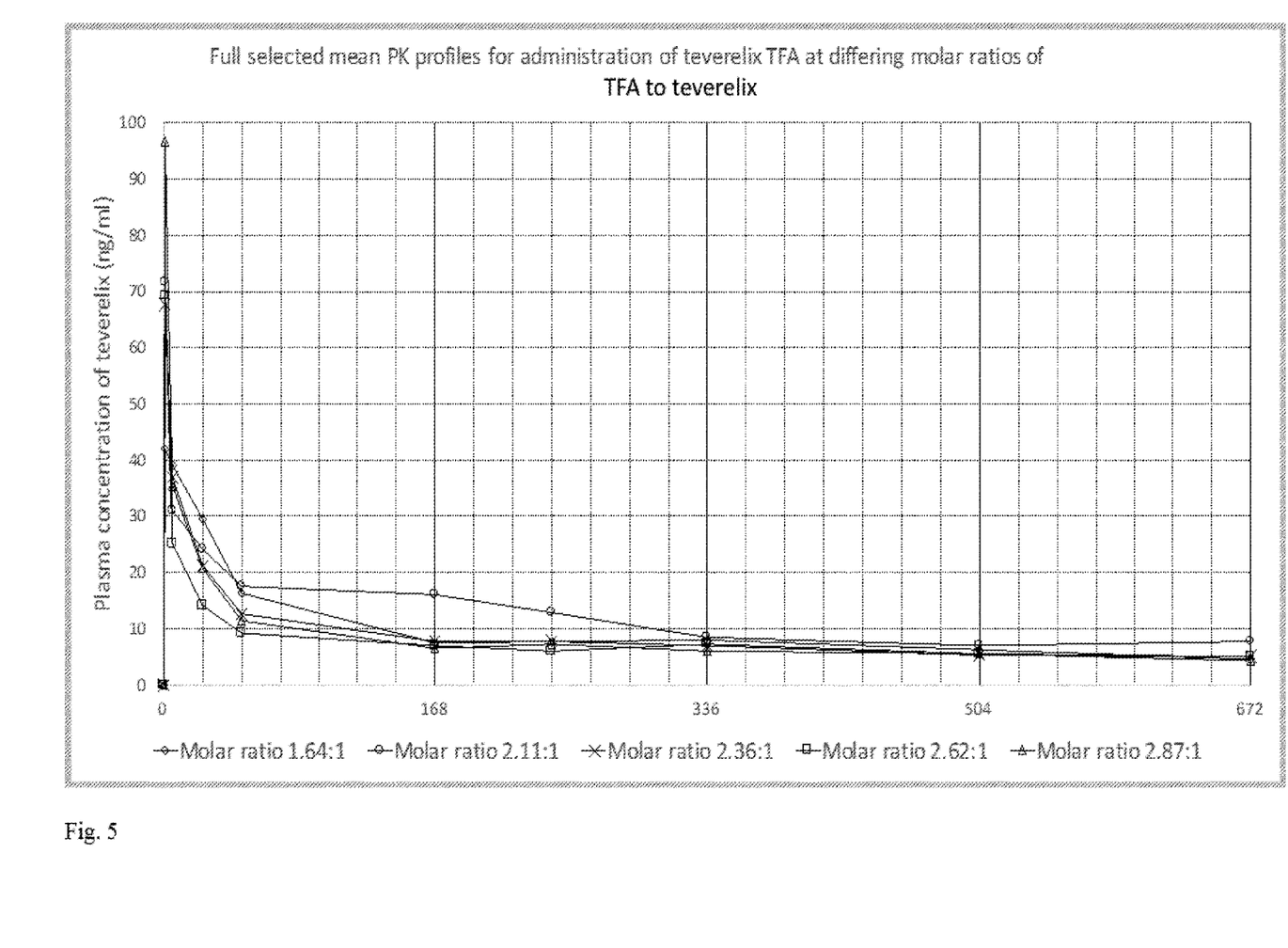

The mean plasma levels in a four weeks period is shown in FIG. 5, and it is clear that the release profile of teverelix is dependent on the molar ratio.

Example 4: Stability of Teverelix in Relation to the Molar Ratio

In order to establish the influence of the molar ratio of teverelix to the counter-ion trifluoroacetate on the stability of teverelix, the following test was performed.

Four batches of teverelix TFA solutions were prepared with differing molar ratios of teverelix to TFA (low: 1:1.7; mid-range: 1:2.16; high 1:2.8; and extreme: 1:4.0) at two concentrations: 10 mg/mL (expressed as base teverelix) and 1 mg/mL (expressed as base teverelix).

A reconstitutable Teverelix TFA composition, supplied as a dried powder, was obtained. The characteristics of the batch are shown in table 9:

TABLE 9

| | |
|---|---|
| Teverelix content | 79.8% |
| TFA content | 13.5% |
| Water content | 3.1% |

The molar ratio of the starting material was determined using the following calculation:

$$\frac{\text{Teverelix content/molecular weight of teverelix}}{\text{TFA content/molecular weight of TFA}} \Rightarrow \frac{79.8/1459}{13.1/144} = \frac{1}{2.16} = 1:2.16$$

The eight batches, one for each of the four molar ratios of 10 mg/ml, and one for each of the four molar ratios of 1 mg/ml, were prepared as follows.

Low Molar Ratio (1:1.7) at 10 mg/mL
1. 0.312 g of teverelix TFA (net weight teverelix) was reconstituted with water for injection, making the suspension up to 3.0 mL to form an 104 mg/mL homogenous milky suspension. Previous investigations demonstrate that at this concentration 96% of the teverelix will form solid teverelix, therefore approximately 300 mg of teverelix will be recovered as solid teverelix following centrifugation.
2. The preparation was immediately centrifuged for 10 minutes at 10,000 rpm (8,500 g) at 4° C.
3. The supernatant from the centrifuged material was discarded. Previous investigations have demonstrated that the solid teverelix has a molar ratio of approximately 1:1.7 teverelix to TFA.
4. The centrifugation pellet was resuspended with water for injection and made up to 30 mL to form a solution of approximately 10 mg/mL and a molar ratio of approximately 1:1.7.

Mid-Molar Range Ratio (1:2.16) at 10 mg/mL
1. 0.1 g of teverelix TFA (net weight teverelix) was reconstituted with water for injection in a 10 mL conical flask to make a solution of 10.0 mL volume to form a solution of teverelix at 10 mg/mL and a molar ratio of 1:2.16 teverelix to TFA.

High Molar Ratio (1:2.8) at 10 mg/mL
1. 0.1 g teverelix TFA (net weight teverelix) was reconstituted with 5 mL of 0.0097 M trifluoroacetic acid in water for injection in a 10 mL conical flask
2. The solution was made up to 10.0 mL with water for injection to form a solution of teverelix at 10 mg/mL and a molar ratio of 1:2.8 teverelix to TFA.

Extreme Molar Ratio (1:4.0) at 10 mg/mL
1. 0.1 g teverelix TFA (net weight teverelix) was reconstituted with 5 mL of 0.0252 M trifluoroacetic acid in water for injection in a 10 mL conical flask
2. The solution was made up to 10.0 mL with water for injection to form a solution of teverelix at 10 mg/mL and a molar ratio of 1:4.0 teverelix to TFA.

Low Molar Ratio (1:1.7) at 1 mg/mL
1. 0.312 g of teverelix TFA (net teverelix) was reconstituted with water for injection, making the suspension up to 3.0 mL to form an 104 mg/mL homogenous milk suspension.
2. The preparation was immediately centrifuged for 10 minutes at 10,000 rpm (8,500 g) at 4° C.
3. The supernatant from the centrifuged material was discarded
3. The centrifugation pellet was resuspended in water for injection (final volume 300 mL) to make up a solution of approximately 1 mg/mL and a molar ratio approximately 1:1.7 teverelix to TFA.
4. 10.0 mL was transferred to a 10 mL conical flask.

Mid-Molar Range Ratio (1:2.16) at 1 mg/mL
1. A 1 mg/mL solution of teverelix TFA in water for injection was prepared High Molar Ratio (1:2.8) at 1 mg/mL
1. 0.010 g teverelix TFA (net weight teverelix) was reconstituted with 5 mL of a 0.001 M trifluoroacetic acid in water for injection in a 10 mL conical flask
2. The volume was completed to 10 mL with WFI Extreme Molar Ratio (1:4.0) at 1 mg/mL
1. 0.010 g teverelix TFA (net weight teverelix) was reconstituted with 5 mL of a 0.0205 M trifluoroacetic acid in water for injection in a 10 mL conical flask
2. The volume was completed to 10 mL with WFI All of the solutions were kept at lab temperature (20° C.) before analyses for teverelix purity.

Samples was taken from each solution in duplicate and analysed for teverelix purity using a conventional RP-HPLC method. The chromatic conditions were as shown in table 10:

TABLE 10

| Column | Phenomenex Aqua C18 150 2.0 mm, 3 μm, 125 Å, LCC-012 |
|---|---|
| Column temperature | 65° C. |
| Autosampler temperature | 4° C. |
| Flow rate | 0.3 ml/min |
| Injection volume | 3 μl |
| Run time | 60 minutes |
| Detection | UV detection, 226 nm |

The purity of teverelix in the solutions after preparation, i.e. at time zero, is shown in table 11:

TABLE 11

| Molar ratio | 10 mg/mL Time 0 | 1 mg/mL Time: 0 |
|---|---|---|
| 1:1.7 | 99.47% | 99.58% |
| 1:2.16 | 99.45% | 99.49% |
| 1:2.8 | 99.48% | 99.48% |
| 1:4.0 | 99.47% | 99.48% |

In order to evaluate the stability over time, the respective solutions were then stored in stoppered glass conical flasks in a chamber at +40° C. and a relative humidity of 75%.

After one month for the 10 mg/mL solutions, and two weeks for the 1 mg/mL solutions, teverelix purity analysis was repeated using the method already described. The purity of the solutions after the relevant period, is presented in table 12 below.

TABLE 12

| Molar ratio | 10 mg/mL Time: 1 month | 1 mg/mL Time: 15 days |
|---|---|---|
| 1:1.7 | 97.49% | 98.92% |
| 1:2.16 | 95.99% | 98.68% |
| 1:2.8 | 93.49% | 98.37% |
| 1:4.0 | 86.16% | 97.97% |

Figure 6:
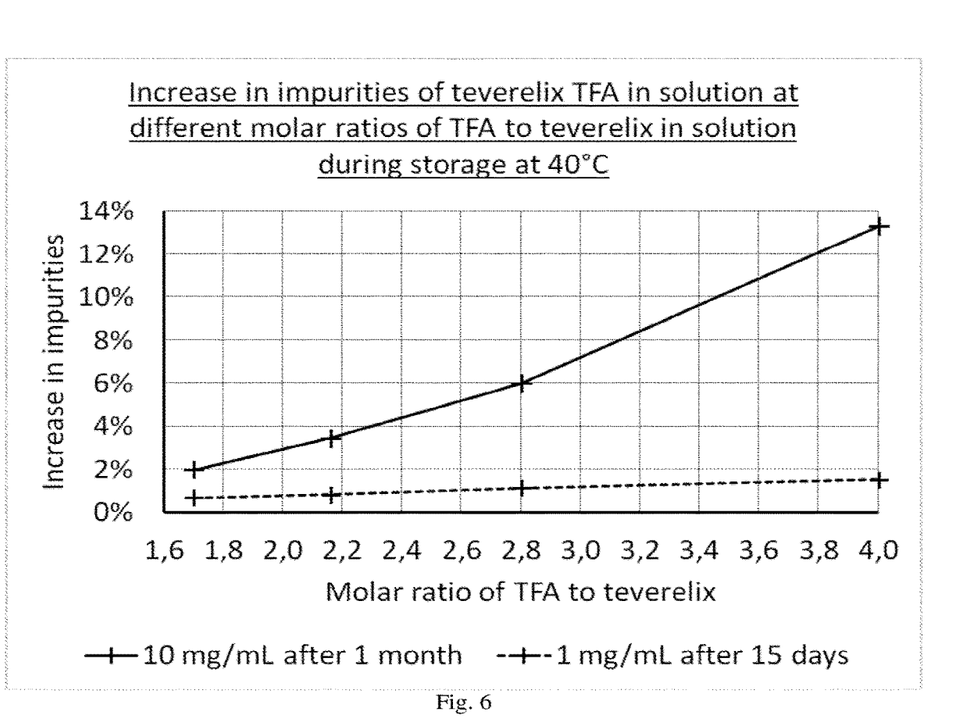
Figure 7:
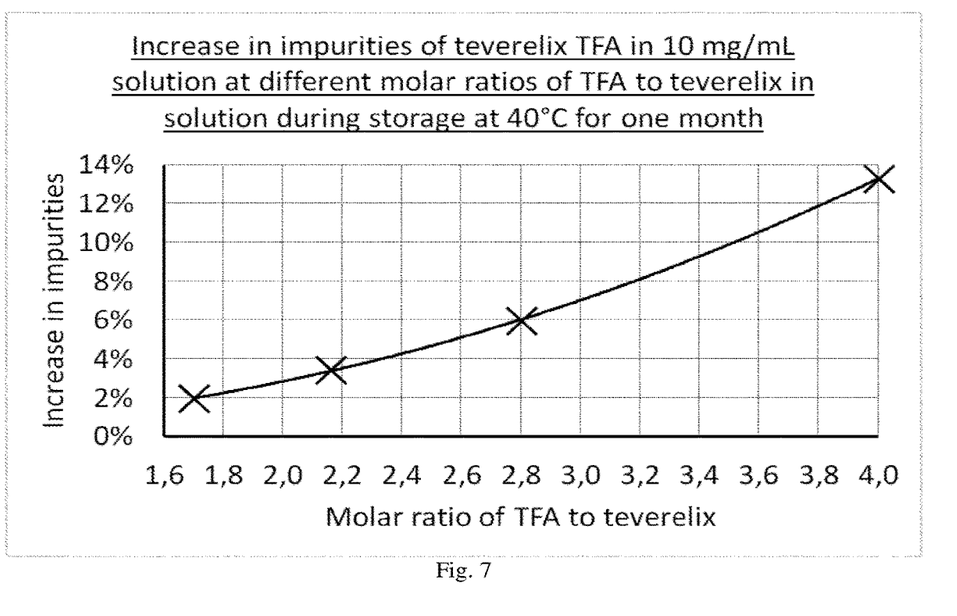

The stability results are shown in FIGS. 6 and 7, and depicts the increase in percentage of impurities during storage according to the molar ratio of the solutions.

From said figures it is clear that higher concentrations of trifluoroacetate in the solutions provides significantly higher concentrations of impurities, thus the results verifies that when teverelix is placed in contact with high concentrations of acid (trifluoroacetate), undesirable degradation products (impurities) will appear in small amounts. Thus, in order to obtain a stable teverelix-TFA formulation, it is important to provide a composition with a low concentration/content of trifluoroacetate, i.e. for each mol of teverelix the molar content of trifluoroacetate should be kept as low as possible.

From FIGS. 6 and 7, it can be seen that when the molar ratio of teverelix to trifluoroacetate is below 1:2.8, (i.e. 1 mol teverelix to 2.8 mol TFA, or less) in the suspension, the level of impurities, i.e. undesirable degradation products e.g. caused by deamidation are kept at an acceptable level.

It is also clear from said figures, that the concentration of teverelix is also relevant for the level of impurities. However, in order to reduce the injections volumes, it is relevant to have suspensions comprising concentrations of teverelix of at least 10 mg/ml preferably at least 30 mg/ml, thus it is not practically possible simply to reduce the concentration of teverelix in the final formulation. However, this factor makes the content of acid (trifluoroacetate) in the composition even more important during storage, as a low level of acid will provide a more stable product.

Thus, for each mole of teverelix the molar content of TFA should be at or between 2.2 and 2.8.

The molar content of TFA at or above 2.2 per mol teverelix are essential for ensuring that the composition/formulation/suspension comprises both soluble and insoluble teverelix, thereby both providing a unique bioavailablity of teverelix, and ensuring that the suspension is easy to administer by subcutaneous and/or intramuscular injection. A molar ratio below 1:2.2. will result in undesirable gel-formation, making the suspension very difficult to inject. Furthermore, the molar content of TFA at or below 2.8 per mole teverelix is relevant for providing a stable teverelix-TFA product, in which the amount of impurities e.g. undesirable deamidated products, is kept at acceptable levels.

The compositions and formulations provided in the present invention is inexpensive to manufacture, and due to the ease of use they also provides a very simple dosage regime.

Modifications and combinations of the above principles and combinations are foreseen within the scope of the present invention.

The invention claimed is:

1. A homogeneous teverelix-trifluoroacetate (TFA) composition having a molar ratio of teverelix (Ac-D-Nal-D-pClPhe-D-Pal-Ser-Tyr-D-Hci-Leu-Lys(iPr)-Pro-D-Ala-NH$_2$) to trifluoroacetate of at least 1:2.2 and at or below 1:2.8, such that for each mole of teverelix in the composition, the composition comprises at least 2.2 mol of trifluoroacetate and at or below 2.8 mol of trifluoroacetate, wherein peak plasma concentration ($C_{max}$) of teverelix after administration of the teverelix-TFA composition is stable relative to a teverelix-TFA composition having a molar ratio of teverelix to trifluoroacetate of below 1:2.2.

2. The teverelix-TFA composition according to claim 1, wherein the amount of insoluble microcrystalline teverelix in said composition is at least 80% based on the weight of the homogeneous teverelix-TFA composition.

3. The teverelix-TFA composition according to claim 1 for use as a medicament.

4. The teverelix-TFA composition according to claim 1 for use in treating a condition or disease related to the release of a gonadotropin hormone.

5. The teverelix-TFA composition according to claim 4, wherein the condition or disease is benign prostatic hyperplasia; acute urinary retention; endometriosis; a cancer comprising prostate, breast, or cervical cancer; chemical castration; a hormone imbalance; an androgen-sensitive condition; an estrogen sensitive condition; or a combination thereof.

6. A pharmaceutical formulation comprising the teverelix-TFA composition according to claim 1.

7. The pharmaceutical formulation according to claim 6 in the form of a microcrystalline homogeneous aqueous suspension, and wherein the molar ratio of teverelix to trifluoroacetate is between 1:2.2 and 1:2.8, such that for each mole of teverelix in the composition, the composition comprises between 2.2 and 2.8 mol of trifluoroacetate.

8. The pharmaceutical formulation according to claim 7, wherein the microcrystalline homogeneous aqueous suspension further comprises an isotonic agent and/or a pharmaceutically acceptable excipient.

9. A package filled with the teverelix-TFA composition according to claim 1 or the pharmaceutical formulation according to claim 6.

10. The package according to claim 9, comprising a unit dosage of the teverelix-TFA composition according to claim 1 or the pharmaceutical formulation according to claim 6.

11. The package according to claim 10, wherein the unit dosage comprises:
an aqueous teverelix-TFA formulation having a molar ratio of teverelix to trifluoroacetate of 1:2.2, such that for each mole of teverelix in the formulation the formulation comprises 2.2 mol of trifluoroacetate, and the concentration of teverelix is between 30 mg/ml and 100 mg/ml.

12. The package according to claim 9, wherein the package is a syringe suitable for providing a subcutaneous and/or intramuscular injection.

13. The package according to claim 12, wherein the volume in the syringe is between 0.4 ml and 1.6 ml.

14. A homogeneous and stable teverelix-trifluoroacetate (TFA) composition having a molar ratio of teverelix (Ac-D-Nal-D-pClPhe-D-Pal-Ser-Tyr-D-Hci-Leu-Lys(iPr)-Pro-D-Ala-NH$_2$) to trifluoroacetate of at least 1:2.4 and at or below 1:2.8, such that for each mole of teverelix in the composition, the composition comprises at least 2.4 mol of trifluoroacetate and at or below 2.8 mol of trifluoroacetate.

* * * * *